United States Patent
Salit et al.

(10) Patent No.: US 11,952,438 B2
(45) Date of Patent: Apr. 9, 2024

(54) 1,3-DIPOLAR COMPOUND COMPRISING AN EPOXIDE GROUP

(71) Applicant: COMPAGNIE GENERALE DES ETABLISSEMENTS MICHELIN, Clermont-Ferrand (FR)

(72) Inventors: Anne-Frédérique Salit, Clermont-Ferrand (FR); Benoît Schnell, Clermont-Ferrand (FR); Sophie Gander, Clermont-Ferrand (FR); Sergey Ivanov, Clermont-Ferrand (FR); Etienne Fleury, Clermont-Ferrand (FR)

(73) Assignee: COMPAGNIE GENERALE DES ETABLISSEMENTS MICHELIN, Clermont-Ferrand (FR)

( * ) Notice: Subject to any disclaimer, the term of this patent is extended or adjusted under 35 U.S.C. 154(b) by 676 days.

(21) Appl. No.: 16/763,456

(22) PCT Filed: Nov. 20, 2018

(86) PCT No.: PCT/FR2018/052913
§ 371 (c)(1),
(2) Date: May 12, 2020

(87) PCT Pub. No.: WO2019/102128
PCT Pub. Date: May 31, 2019

(65) Prior Publication Data
US 2021/0171670 A1 Jun. 10, 2021

(30) Foreign Application Priority Data
Nov. 21, 2017 (FR) .................. 1760957

(51) Int. Cl.
| | |
|---|---|
| *C08C 19/06* | (2006.01) |
| *B60C 1/00* | (2006.01) |
| *B60C 11/00* | (2006.01) |
| *C07D 303/46* | (2006.01) |
| *C08F 279/02* | (2006.01) |
| *C08K 3/36* | (2006.01) |

(52) U.S. Cl.
CPC ............ *C08C 19/06* (2013.01); *B60C 1/0016* (2013.01); *B60C 11/0008* (2013.01); *C07D 303/46* (2013.01); *C08F 279/02* (2013.01); *C08K 3/36* (2013.01); *B60C 2011/0025* (2013.01)

(58) Field of Classification Search
CPC ... C08C 19/06; B60C 1/0016; B60C 11/0008; B60C 2011/0025; C07D 303/46; C08F 279/02; C08K 3/36
USPC ........................................................ 558/434
See application file for complete search history.

(56) References Cited

U.S. PATENT DOCUMENTS

| | | | |
|---|---|---|---|
| 3,941,751 A | | 3/1976 | Breslow |
| 5,710,290 A | * | 1/1998 | Lysenko ............... C07C 291/06 549/546 |
| 2012/0046418 A1 | | 2/2012 | Seo et al. |

OTHER PUBLICATIONS

International Search Report and Written Opinion corresponding to PCT/FR2018/052913 dated Mar. 11, 2019.
Jacques M. Lemmens, et al., Journal of Organic Chemistry, Synthesis of .alpha.,.beta.-epoxyacyl azides and their rearrangement to epoxy isocyanates and 3-and 4-oxazolin-2-ones, Jun. 1, 1984 American Chemical Society, US, vol. 49, Nr. 12, pp. 2231-2235; XP055486649.
Stupp H, et al., Synthesis of Aryl Azide Analogues of Insect Juvenile Hormones as Reagents for the Photoaffinity Labeling of Juvenile Hormone Binding Proteins; XP055486651.
Stuart Lang, et al., Amination of Arenes through Electron-Deficient Reaction Cascades of Aryl Epoxyazides; Organic Letters, Oct. 1, 2003—ISSN 1523-7060, vol. 5, Nr:20, pp. 3655-3658; XP055486652.

* cited by examiner

*Primary Examiner* — Kelechi C Egwim
(74) *Attorney, Agent, or Firm* — Dickinson Wright PLLC

(57) ABSTRACT

A 1,3-dipolar compound including an epoxide group is provided. The epoxide group is a 3-membered ether ring in which a first member is a carbon atom having an attachment to the dipole of the 1,3-dipolar compound and a second member is a tertiary or quaternary carbon. The use of the 1,3-dipolar compound in the modification of a diene polymer makes it possible to improve the rupture properties of a rubber composition comprising the modified polymer, without the expense of its hysteresis properties, while at the same time improving its implementation.

13 Claims, No Drawings

1,3-DIPOLAR COMPOUND COMPRISING AN EPOXIDE GROUP

This application is a 371 national phase entry of PCT/FR2018/052913 filed on 20 Nov. 2018, which claims benefit of French Patent Application No. 1760957, filed 21 Nov. 2017, the entire contents of which are incorporated herein by reference for all purposes.

BACKGROUND

1. Technical Field

The field of the present invention is that of agents for modifying diene polymers, more particularly that of modifying agents for grafting epoxide functions onto a diene polymer.

2. Related Art

Patent application US 2012/0046418 A1 discloses a diene elastomer being modified by reacting a 1,3-dipolar compound bearing a glycidyl group with the diene units of the elastomer. The modification results in a diene elastomer bearing glycidyl side groups being obtained. These elastomers thus obtained may be used crosslinked in a rubber composition, the presence of the glycidyl side groups making it possible to crosslink the diene elastomer in the presence of a crosslinking agent other than sulfur. It turns out that the elastomers thus modified give the rubber composition which contains them degraded rupture properties.

Now, a crosslinked rubber composition must have good rupture properties in order to be able to be used in a semi-finished article for tyres. Specifically, during rolling, a tyre is subjected to high stresses and to great strains, given that it must also have the lowest possible rolling resistance.

SUMMARY

The Applicant has discovered, surprisingly, that the use of 1,3-dipolar compounds bearing a particular substituted epoxide group in the modification of diene elastomers makes it possible to improve the rupture properties of a rubber composition comprising such modified elastomers, without this being at the expense of its hysteresis properties, while at the same time improving its implementation.

A first subject of the invention is a 1,3-dipolar compound including an epoxide group, the epoxide group being a 3-membered ether ring in which a first member is a carbon atom having an attachment to the dipole of the 1,3-dipolar compound and a second member is a tertiary or quaternary carbon.

Another subject of the invention is a process for a diene polymer, notably a diene elastomer, via a grafting reaction, which comprises the reaction of a starting diene polymer and of a 1,3-dipolar compound in accordance with the invention.

The invention also relates to a polymer, notably a diene elastomer, which may be obtained via the process in accordance with the invention.

The invention also relates to a rubber composition which comprises a reinforcing filler, a crosslinking system and a diene elastomer in accordance with the invention.

Another subject of the invention is a tyre which comprises a rubber composition in accordance with the invention.

I. DETAILED DESCRIPTION

In the present description, unless expressly indicated otherwise, all the percentages (%) shown are mass percentages. The abbreviation "phr" means parts by weight per hundred parts of elastomer (of the total of the elastomers, if several elastomers are present).

Furthermore, any interval of values denoted by the expression "between a and b" represents the range of values greater than "a" and less than "b" (i.e. limits a and b excluded), whereas any interval of values denoted by the expression "from a to b" means the range of values extending from "a" up to "b" (i.e. including the strict limits a and b).

The compounds mentioned in the description may be of fossil or biobased origin. In the latter case, they may be partially or totally derived from biomass or may be obtained from renewable starting materials derived from biomass. Polymers, plasticizers, fillers, etc., are also concerned.

The term "1,3-dipolar compound" is understood according to the definition given by the IUPAC. By definition, it contains a dipole.

In the present patent application, the term "carbon-based group" means a group which contains one or more carbon atoms. The term "group of atoms" also means a group consisting of a sequence of several covalently bonded atoms.

In the present patent application, a carbon atom which is a member of the epoxide ring is termed a tertiary carbon when the carbon atom is directly covalently bonded to two carbon atoms, of which one is also a member of the epoxide ring, and to the oxygen atom which is a member of the epoxide ring. A carbon atom which is a member of the epoxide ring is termed a quaternary carbon when the carbon atom is directly covalently bonded to three carbon atoms, of which one is also a member of the epoxide ring, and to the oxygen atom which is a member of the epoxide ring.

An essential feature of the 1,3-dipolar compound is that it includes, in addition to the dipole, an epoxide group. In a known manner, an epoxide group is a 3-membered ether ring, two members of which are two carbon atoms and the third member is an oxygen atom. The epoxide group that is useful for the purposes of the invention is a 3-membered ether ring, of which a first member is a carbon atom having an attachment to the dipole and a second member is a tertiary or quaternary carbon. Preferably, the epoxide group is of formula (I),

In which formula (I) the symbol * represents an attachment to the dipole; the symbols $X^1$, $X^2$ and $X^3$, which may be identical or different, represent a hydrogen atom or a substituent group, and at least one of the symbols $X^1$, $X^2$ and $X^3$ is other than a hydrogen atom.

According to a preferential embodiment, $X^3$ represents a hydrogen atom, which means that the first member of the epoxide ring is a tertiary carbon.

According to another preferential embodiment, $X^1$ represents a substituent group and $X^2$ represents a hydrogen atom, in which case the second member of the epoxide ring is a tertiary carbon.

According to another preferential embodiment of the invention, $X^1$ and $X^2$ each represent a substituent group, in which case the second member of the epoxide ring is a quarternary carbon.

Preferably, the substituent group represented by the symbols $X^1$, $X^2$ or $X^3$ is a carbon-based group, in particular a hydrocarbon-based group. The substituent group may be aliphatic or aromatic, and linear, branched or cyclic. Substituent groups that are particularly suitable are alkyls and aryls, more particularly alkyls containing 1 to 6 carbon atoms, preferably methyl, or aryls containing 6 to 12 carbon atoms, preferably phenyl.

Preferably, the dipole of the 1,3-dipolar compound in accordance with the invention is a dipole containing at least one nitrogen atom, more preferentially a dipole chosen from the group consisting of the nitrile oxide dipole, the nitrone dipole and the nitrile imine dipole. In other words, the 1,3-dipolar compound is more preferentially chosen from the group consisting of nitrile oxides, nitrones and nitrile imines. Advantageously, the 1,3-dipolar compound is a nitrile oxide.

According to one embodiment, the 1,3-dipolar compound comprises a benzene nucleus substituted with the dipole of the 1,3-dipolar compound and preferably also substituted ortho to the dipole. Very advantageously, the 1,3-dipolar compound is an aromatic nitrile oxide, i.e. an aromatic compound substituted with a nitrile oxide dipole (—C≡N→O). Better still, the 1,3-dipolar compound is an aromatic nitrile monoxide, which corresponds to a compound which contains only one nitrile oxide dipole and which is an aromatic compound substituted with the nitrile oxide dipole.

According to one very specific embodiment of the invention, the 1,3-dipolar compound contains a unit of formula (II) in which four of the five symbols R1 to R5, which may be identical or different, are each an atom or a group of atoms, and the fifth symbol represents a carbon-based chain allowing attachment to the epoxide group, given that at least one from among R1 and R5 is other than a hydrogen atom.

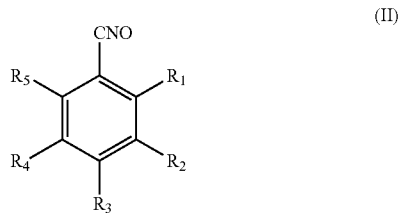

(II)

The term "group of atoms" means a sequence of atoms covalently bonded to form a chain. Two groups Ri and Ri+1, for i which is an integer ranging from 1 to 4, may form, together with the carbon atoms of the benzene nucleus to which they are attached, a ring.

Preferably, R1, R3 and R5 each represent a hydrocarbon-based group and R2 or R4 represents the fifth symbol. More preferentially, R1, R3 and R5 each represent an alkyl, even more preferentially a methyl or an ethyl.

The carbon-based chain represented by the fifth symbol may be aliphatic or aromatic, and linear, branched or cyclic, preferably saturated. The fifth symbol preferentially represents a carbon-based chain interrupted with one or more heteroatoms, preferably oxygen. The term "carbon-based chain" means a chain which comprises one or more carbon atoms. The carbon-based chain may be a hydrocarbon-based chain. The carbon-based chain may comprise one or more ether functions; in particular, the fifth symbol comprises a —CH₂O— unit, the methylene group being attached to the epoxide group.

Very advantageously, the 1,3-dipolar compound is a compound of formula (III), (IV) or (V).

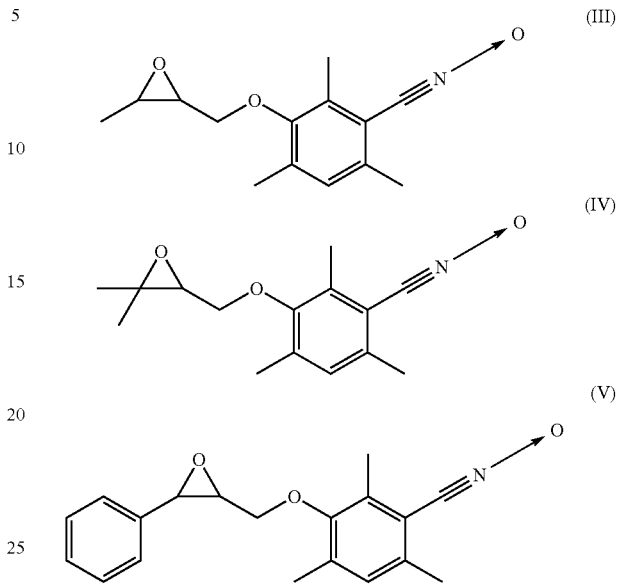

The 1,3-dipolar compound in accordance with the invention may be used for grafting one or more diene polymers, notably elastomers, present in a rubber composition. It may be used for grafting one or more epoxide groups onto the polymer, preferably several groups. The content of 1,3-dipolar compound may vary within a wide range depending on the envisaged application of the rubber composition. According to any one of the embodiments of the invention, the 1,3-dipolar compound is preferentially introduced into the rubber composition in a content ranging from 0.01 to 5 mol %, more preferentially from 0.01 to 1 mol % and even more preferentially from 0.1 to 1 mol %. This content expressed as a molar percentage is equivalent to the number of moles of 1,3-dipolar compound per 100 mol of diene monomer units of diene polymer to be grafted. The term "diene monomer unit" means any unit which results from the insertion of a diene into a polymer chain and which contains a carbon-carbon double bond.

The grafting proceeds from a [2+3] cycloaddition reaction of the dipole on a carbon-carbon double bond according to a well-known mechanism, it being possible to conduct the reaction in bulk or in a solution. When the grafting is performed in bulk it is preferentially performed in the presence of an antioxidant. The grafting in bulk is performed for example in an internal mixer or an external mixer, such as an open mill, either at a temperature of the external mixer or of the internal mixer of less than 60° C., followed by a step of a grafting reaction under a press or in an oven at temperatures ranging from 80° C. to 200° C., or at a temperature of the external mixer or of the internal mixer of greater than 60° C., without subsequent heat treatment. The grafting of the 1,3-dipolar compound on the polymer may be performed prior to the introduction of the polymer into the rubber composition, or during the manufacture of the composition.

The term "diene polymer" is to be understood to mean a polymer comprising diene monomer units bearing a carbon-carbon double bond, in particular 1,3-diene monomer units.

The starting diene polymer which may be modified via the process in accordance with the invention may be:
  (a) any homopolymer of a conjugated diene monomer, notably any homopolymer obtained by polymerization of a conjugated diene monomer containing from 4 to 12 carbon atoms;
  (b) any copolymer obtained by copolymerization of one or more conjugated dienes with each other or with one or more vinylaromatic compounds containing from 8 to 20 carbon atoms;
  (c) a ternary copolymer obtained by copolymerization of ethylene, of an α-olefin containing from 3 to 6 carbon atoms with a non-conjugated diene monomer containing from 6 to 12 carbon atoms, for instance the elastomers obtained from ethylene and propylene with a non-conjugated diene monomer of the abovementioned type, notably such as 1,4-hexadiene, ethylidenenorbornene or dicyclopentadiene;
  (d) a copolymer of isobutene and of isoprene (butyl rubber) and also the halogenated versions, in particular chlorinated or brominated versions, of this type of copolymer;
  (e) any copolymer obtained by copolymerization of one or more conjugated dienes with ethylene, an acyclic aliphatic α-monoolefin containing from 3 to 18 carbon atoms or a mixture thereof, for instance those described in WO 2005/028526, WO 2004/035639 and WO 2007/054224.

Preferably, the starting diene polymer is a 1,3-butadiene homopolymer, an isoprene homopolymer, a 1,3-butadiene copolymer, an isoprene copolymer or mixtures thereof. The starting diene polymer is more preferentially a diene elastomer, notably a 1,3-butadiene homopolymer, an isoprene homopolymer, a 1,3-butadiene copolymer, an isoprene copolymer or mixtures thereof.

The modified polymer in accordance with the invention which may be obtained according to the process in accordance with the invention is preferably a diene elastomer, i.e. an elastomer which contains both diene units and epoxide groups described according to any one of the embodiments of the invention. The modified elastomer may be used in a rubber composition, notably for tyres. In this case, the rubber composition contains, in addition to the modified elastomer, a reinforcing filler and a crosslinking system. The rubber composition may be in uncured form (before crosslinking) or in cured form (after crosslinking).

The composition of the invention includes any type of "reinforcing" filler known for its abilities to reinforce a rubber composition which can be used in the manufacture of tyres, for example an organic filler, such as carbon black, a reinforcing inorganic filler, such as silica, with which a coupling agent is combined in a known manner, or else a mixture of these two types of filler. Such a reinforcing filler typically consists of nanoparticles, the (mass-) average size of which is less than a micrometre, generally less than 500 nm, most usually between 20 and 200 nm, in particular and more preferentially between 20 and 150 nm.

According to a particular embodiment of the invention, the reinforcing filler comprises an inorganic filler, preferentially a silica. According to this embodiment of the invention, the reinforcing inorganic filler represents more than 50% by mass relative to the mass of the reinforcing filler of the rubber composition. The reinforcing inorganic filler is then said to be predominant.

When it is combined with a predominant reinforcing inorganic filler, such as silica, the carbon black is preferably used at a content of less than 20 phr, more preferentially of less than 10 phr (for example, between 0.5 and 20 phr, notably between 2 and 10 phr). Within the intervals indicated, the colouring properties (black pigmenting agent) and UV-stabilizing properties of the carbon blacks are beneficial, without, moreover, adversely affecting the typical performance qualities contributed by the reinforcing inorganic filler.

Preferentially, the content of total reinforcing filler is between 30 and 160 phr, more preferentially between 40 phr and 160 phr. Below 30 phr, the reinforcement of the rubber composition is insufficient to contribute an appropriate level of cohesion or wear resistance of the rubber component of the tyre comprising this composition. Even more preferentially, the content of total reinforcing filler is at least 50 phr. Above 160 phr, there is a risk of increase in the hysteresis and thus in the rolling resistance of the tyres. For this reason, the content of total reinforcing filler is preferably within a range extending from 50 to 120 phr, notably for use in a tyre tread. Any one of these ranges of content of total reinforcing filler may apply to any one of the embodiments of the invention.

In order to couple the reinforcing inorganic filler to the diene elastomer, use is made, in a well-known manner, of an at least difunctional coupling agent, notably a silane, (or bonding agent) intended to provide a satisfactory connection, of chemical and/or physical nature, between the inorganic filler (surface of its particles) and the diene elastomer. Use is made in particular of organosilanes or polyorganosiloxanes which are at least difunctional. More particularly, use is made of silane polysulfides, referred to as "symmetrical" or "asymmetrical" depending on their specific structure, as described, for example, in patent applications WO 03/002648 (or US 2005/016651) and WO 03/002649 (or US 2005/016650). As examples of polysulfide silanes, mention will be made more particularly of bis(($C_1$-$C_4$)alkoxyl($C_1$-$C_4$)alkylsilyl($C_1$-$C_4$)alkyl) polysulfides (notably disulfides, trisulfides or tetrasulfides), for instance bis(3-trimethoxysilylpropyl) or bis(3-triethoxysilylpropyl) polysulfides. Among these compounds, use is made in particular of bis(3-triethoxysilylpropyl) tetrasulfide, abbreviated to TESPT, of formula $[(C_2H_5O)_3Si(CH_2)_3S_2]_2$, or bis(triethoxysilylpropyl) disulfide, abbreviated to TESPD, of formula $[(C_2H_5O)_3Si(CH_2)_3S]_2$.

The content of coupling agent is advantageously less than 20 phr, it being understood that it is generally desirable to use as little as possible thereof. Typically, the content of coupling agent represents from 0.5% to 15% by weight relative to the amount of inorganic filler. Its content is preferentially between 0.5 and 12 phr, more preferentially within a range extending from 3 to 10 phr. This content is readily adjusted by a person skilled in the art depending on the content of inorganic filler used in the composition.

The rubber composition in accordance with the invention may also contain, in addition to the coupling agents, coupling activators, agents for covering the inorganic fillers or more generally processing aids that are capable, in a known manner, by means of improving the dispersion of the filler in the rubber matrix and of lowering the viscosity of the compositions, of improving their ability to be processed in the uncured state.

The rubber composition in accordance with the invention may also include all or some of the usual additives customarily used in elastomer compositions intended to constitute external mixtures for finished rubber articles, such as tyres, in particular for treads, for instance plasticizers or extending oils, pigments, protective agents, such as antiozone waxes, chemical antiozonants, antioxidants, antifatigue agents, reinforcing resins (such as resorcinol or bismaleimide), methylene acceptors (for example phenolic novolac resin) or methylene donors (for example HMT or H3M), as described, for example, in patent application WO 02/10269, a crosslinking system, vulcanization accelerators or retardants, vulcanization activators. The crosslinking system is preferably based on sulfur, but it may be based on polyacids, notably diacids as described in the patent applications WO 2014/095582 and WO 2014/095585.

The rubber composition in accordance with the invention is manufactured in appropriate mixers, using two successive phases of preparation well known to those skilled in the art: a first phase of thermomechanical working or kneading ("non-productive" phase) at high temperature, up to a maximum temperature of between 130° C. and 200° C., followed by a second phase of mechanical working ("productive" phase) down to a lower temperature, typically below 110° C., for example between 40° C. and 100° C., during which finishing phase the crosslinking system is incorporated.

The rubber composition in accordance with the invention may either be in the uncured state (before crosslinking or vulcanization) or in the cured state (after crosslinking or vulcanization). It is preferentially used in a tyre, for example as a semi-finished article, in particular a tread.

The abovementioned characteristics of the present invention, and also others, will be understood more clearly on reading the following description of several implementational examples of the invention, given as non-limiting illustrations.

II. IMPLEMENTATIONAL EXAMPLES

II.1—Measurements and Tests Used

NMR Analysis

The structural analysis and the determination of the molar purities of the molecules synthesized are performed by NMR analysis. The spectra are acquired on a 400 MHz Brüker Avance 3 spectrometer equipped with a 5 mm BBFO Z-grad "broad band" probe. The quantitative $^1$H NMR experiment uses a simple 30° pulse sequence and a repetition time of 3 seconds between each of the 64 acquisitions. The samples are dissolved in deuterated dimethyl sulfoxide (DMSO). This solvent is also used for the lock signal. Calibration is performed on the signal of the protons of the deuterated DMSO at 2.44 ppm relative to a TMS reference at 0 ppm. The $^1$H NMR spectrum coupled with the 2D $^1$H/$^{13}$C HSQC and $^1$H/$^{13}$C HMBC experiments enable the structural determination of the molecules (cf. tables of assignments). The molar quantifications are performed from the quantitative 1D $^1$HNMR spectrum.

The determination of the molar content of grafted nitrile oxide compound is performed by NMR analysis. The spectra are acquired on a 500 MHz Bruker spectrometer equipped with a "5 mm BBFO Z-grad CryoProbe". The quantitative $^1$H NMR experiment uses a simple 30° pulse sequence and a repetition time of 5 seconds between each acquisition. The samples are dissolved in deuterated chloroform (CDCl$_3$) with the aim of obtaining a "lock" signal.

2D NMR experiments made it possible to confirm the nature of the grafted unit by means of the chemical shifts of the carbon atoms and protons.

Tensile Tests

The elongations at break and the breaking stresses are measured by means of tensile tests according to the French standard NF T 46-002 of September 1988. All these tensile measurements are performed under the standard conditions of temperature (23±30 2° C.) and hygrometry (50±5% relative humidity), according to the French standard NF T 40-101 (December 1979).

Dynamic Properties

The dynamic properties tan (δ)max are measured on a viscosity analyser (Metravib VA4000) according to Standard ASTM D 5992-96. The response of a sample of vulcanized composition (cylindrical test specimen with a thickness of 4 mm and a cross section of 400 mm$^2$), subjected to a simple alternating sinusoidal shear stress, at a frequency of 10 Hz, under standard temperature conditions (23° C.) according to standard ASTM D 1349-99, is recorded. A strain amplitude sweep is performed from 0.1% to 100% (outward cycle), and then from 100% to 0.1% (return cycle). The results exploited are the complex dynamic shear modulus (G*) at 25% strain, the loss factor tan (δ) and the difference in modulus (ΔG*) between the values at 0.1% and 100% strain (Payne effect). For the return cycle, the maximum value of tan (δ) observed, denoted tan (δ)max, is indicated.

Rheometry

The measurements are performed at 150° C. with an oscillating disc rheometer, according to the standard DIN 53529—Part 3 (June 1983). The measurements are processed according to the standard DIN 53529—Part 2 (March 1983). The change in the rheometric torque as a function of time describes the change in the stiffening of the composition as a result of the vulcanization reaction and thus makes it possible to monitor the vulcanization progress. The minimum torque value Cmin is measured for each composition. The Cmin is representative of the viscosity in the uncured state (before vulcanization) of the rubber composition and makes it possible to evaluate the processability of the rubber composition.

II.2—Synthesis of the 1,3-Dipolar Compounds

The following 1,3-dipolar compounds D-1, D-2, D-3 and D-4, respectively, were prepared.

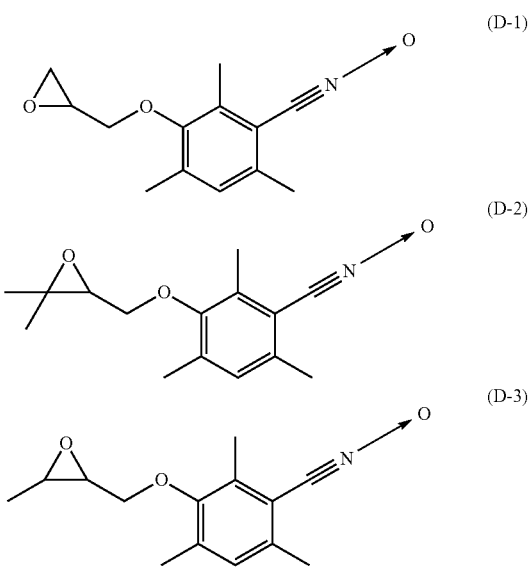

(D-4)

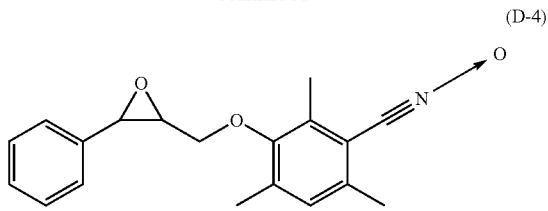

Synthesis of 3-hydroxy-2,4,6-trimethylbenzaldehyde (Target 1)

Target compound 1 (or A) is a common precursor used in the synthesis of some of the 1,3-dipolar compounds. It is synthesized according to the following scheme:

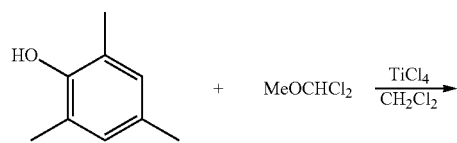

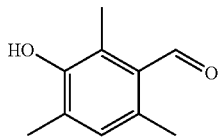

Target compound 1 may be obtained according to a procedure described in the article Yakubov, A. P.; Tsyganov, D. V.; Belen'kii, L. I.; Krayushkin, M. M. *Bulletin of the Academy of Sciences of the USSR, Division of Chemical Science* (*English Translation*); vol. 40; nb. 7.2; (1991); pages 1427-1432; *Izvestiya Akademii Nauk SSSR, Seriya Khimicheskaya*; nb. 7; (1991); pages 1609-1615.

Synthesis of 2,4,6-trimethyl-3-(oxiran-2-ylmethoxy)benzonitrile Oxide (D-1)

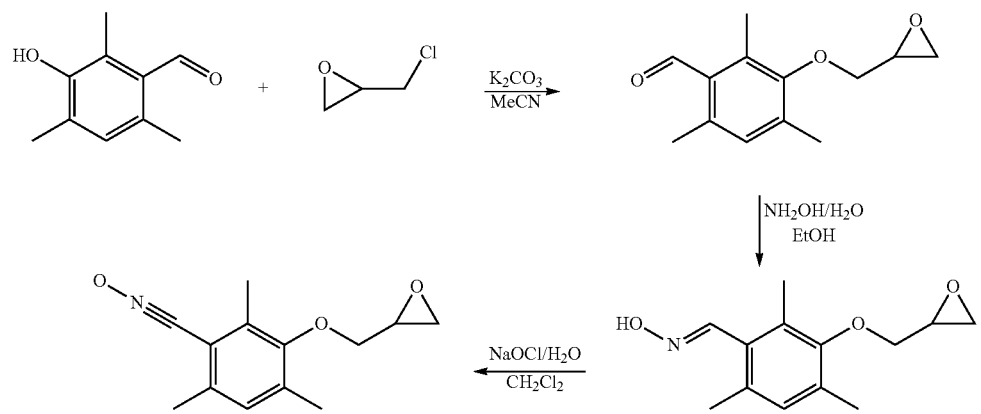

Synthesis of 2,4,6-trimethyl-3-(oxiran-2-ylmethoxy)benzaldehyde (Target 2)

Potassium carbonate (50.50 g, 0.365 mol) is added to a mixture of 3-hydroxy-2,4,6-trimethylbenzaldehyde (40.00 g, 0.244 mol) and epichlorohydrin (56.35 g, 0.609 mol) in acetonitrile (100 ml). The reaction medium is stirred at 60° C. for 3 hours and then at 70° C. for 2.5-3 hours. After returning to 40-50° C., the reaction mixture is diluted with a mixture of water (250 ml) and ethyl acetate (250 ml) and then kept stirring for 10 minutes. The organic phase is separated out and washed with water (4 times with 125 ml). The solvent is evaporated off under reduced pressure ($T_{both}$ 37° C., 40 mbar). A red oil (66.43 g) is obtained.

The second reaction product, 3,3'-((2-hydroxypropane-1,3-diyl)bis(oxy))bis(2,4,6-trimethylbenzaldehyde), is separated from the target product 2 by chromatography on a column of silica (eluent: ¼ ethyl acetate/petroleum ether). After recovering the fractions of the target product 2, the solvents are evaporated off under reduced pressure ($T_{bath}$ 36°C., 21 mbar). Petroleum ether (120 ml) is added to the residue and the suspension is kept stirring at −18° C. for 2 hours. The precipitate is filtered off, washed on the filter with petroleum ether (40/60) (three times 25 ml) and finally dried under atmospheric pressure at room temperature for 10-15 hours. A white solid (40.04 g, yield by mass of 75%) with a melting point of 52° C. is obtained. The molar purity is greater than 99% ($^1$H NMR).

Assignment Table

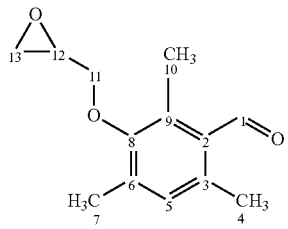

| | δ $^1$H (ppm) | δ $^{13}$C (ppm) |
|---|---|---|
| 1 | 10.37 | 193.3 |
| 2 | / | 131.1 |
| 3 | / | 132.8 |
| 4 | 2.4 | 19.2 |
| 5 | 6.94 | 131.3 |
| 6 | / | 136.3 |
| 7 | 2.2 | 16.1 |
| 8 | / | 153.4 |
| 9 | / | 135.7 |
| 10 | 2.4 | 11.7 |
| 11 | 3.50/4.00 | 73.4 |
| 12 | 3.29 | 49.6 |
| 13 | 2.60/2.76 | 42.9 |

Solvent DMSO

Synthesis of 2,4,6-trinnethyl-3-(oxiran-2-yl-methoxy)benzaldehyde Oxime (Target 3)

A solution of hydroxylamine (16.81 g, 0.254 mol, 50% in water, Aldrich) in ethanol (75 ml) is added at room temperature to a solution of 2,4,6-trimethyl-3-(oxiran-2-yl-methoxy)benzaldehyde (46.70 g, 0.212 mol) in ethanol (750 ml). The reaction medium is stirred at 23° C. (T$_{bath}$) for 3 hours. After evaporating off the solvent (T$_{bath}$ 24° C., 35 mbar), petroleum ether (40/60) (150 ml) is added. The precipitate is filtered off and washed on the filter with petroleum ether (100 ml). The crude product is dissolved in a mixture of ethyl acetate (650 ml) and petroleum ether (650 ml) at room temperature and this solution is filtered on a bed of silica gel (Ø9 cm, 2.0 cm of SiO$_2$).

The solvents are evaporated off (T$_{bath}$ 22-24° C.) and the target product 3 is dried at atmospheric pressure at room temperature. A white solid (43.81 g, yield by mass of 88%) with a melting point of 77° C. is obtained. The molar purity is greater than 99% ($^1$H NMR).

Assignment Table

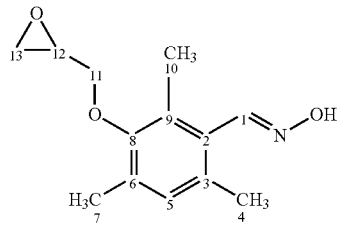

| | δ $^1$H (ppm) | δ $^{13}$C (ppm) |
|---|---|---|
| 1 | 8.2 | 147.3 |
| 2 | / | 129.1 |
| 3 | / | 129.2 |
| 4 | 2.18 | 20.1 |
| 5 | 6.85 | 130.2 |
| 6 | / | 130.3 |
| 7 | 2.15 | 15.7 |
| 8 | / | 153.1 |
| 9 | / | 131.7 |
| 10 | 2.18 | 13.1 |
| 11 | 3.48/3.96 | 73.3 |
| 12 | 3.27 | 49.6 |
| 13 | 2.60/2.76 | 42.8 |

Solvent DMSO

Synthesis of 2,4,6-trimethyl-3-(oxiran-2-ylmethoxy)benzonitrile oxide (D-1)

An aqueous solution of NaOcl in water (62.9 g active Cl/l) (126 ml) is added dropwise over 10-15 minutes to a solution of 2,4,6-trimethyl-3-(oxiran-2-ylmethoxy)benzaldehyde oxime (17.00 g, 0.072 mol) in dichloromethane (350 ml) cooled to 3° C. The temperature of the reaction medium remains between 3 and 5° C. The reaction medium is then stirred for 1 hour at a temperature of 3-5° C. The aqueous phase is separated out and extracted with dichloromethane (25 ml). The combined organic phases are washed with water (three times 75 ml). The solvent is evaporated off under reduced pressure (T$_{bath}$ 22° C., 35 mbar). Petroleum ether (40/60) (90 ml) is added to this residue and the suspension is kept stirring at room temperature for 10-12 hours. The precipitate is filtered off, washed on the filter with petroleum ether (three times 30 ml) and finally dried at atmospheric pressure at room temperature for 10-15 hours. A white solid (15.12 g, yield by weight of 90%) with a melting point of 63° C. is obtained. The molar purity is greater than 99% ($^1$H NMR).

Assignment Table

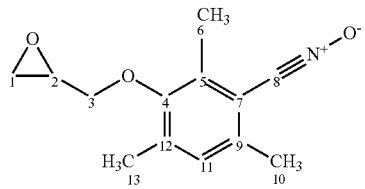

| | δ $^1$H (ppm) | δ $^{13}$C (ppm) |
|---|---|---|
| 1 | 2.59/2.76 | 43.0 |
| 2 | 3.28 | 49.6 |

13
-continued
| | δ ¹H (ppm) | δ ¹³C (ppm) |
|---|---|---|
| 3 | 3.51/4.03 | 73.5 |
| 4 | / | 153.0 |
| 5 | / | 136.3 |
| 6 | 2.27 | 14.3 |
| 7 | / | 111.7 |
| 8 | / | / |
| 9 | / | 134.4 |
| 10 | 2.18 | 15.9 |
| 11 | 7.01 | 129.9 |
| 12 | / | 134.0 |
| 13 | 2.27 | 19.5 |
Solvent DMSO
Synthesis of 2,4,6-trimethyl-3-(3-(3,3-dimethyloxiran-2-yl)propoxy]benzonitrile oxide (D-2)
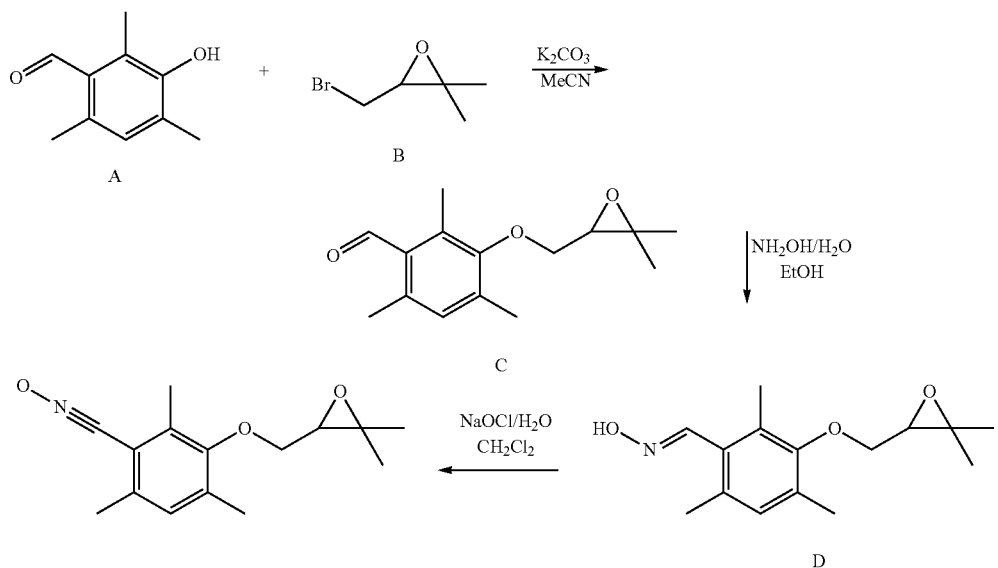
Synthesis of 3-(bromomethyl)-2,2-dimethyloxirane (B)
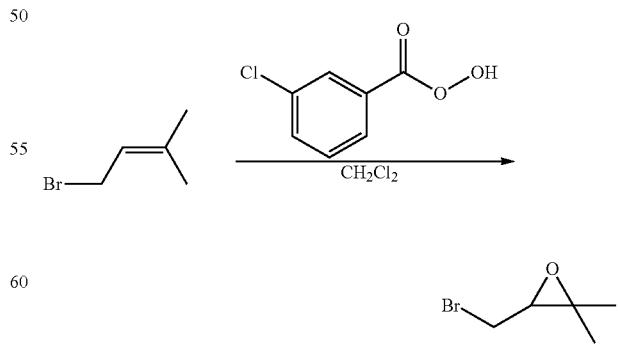
Compound B may be obtained according to a procedure described in the article Shimizu, Hitoshi et al.; *Organic Process Research & Development*, 9(3), 278-287; 2005

Synthesis of 3-(3,3-dimthyloxiran-2-yl)methoxy)-2,4,6-trimethylbenzaldehyde (C)

Potassium carbonate (12.12 g, 0.877 mol) is added to a mixture of 3-hydroxy-2,4,6-trimethylbenzaldehyde (19.20 g, 0.117 mol) and 3-(bromomethyl)-2,2-dimethyloxirane (19.30 g, 0.117 mol) in acetonitrile (50 ml). The reaction medium is stirred at 60° C. ($T_{bath}$) for 10-11 hours. After returning to room temperature, the reaction mixture is diluted with a mixture of water (700 ml) and ethyl acetate (100 ml) and stirred for 10 minutes. The aqueous phase is separated out and extracted with ethyl acetate (three times 75 ml). The combined organic phases are washed twice with NaOH solution (8.0 g in 100 ml of water) and with water (five times 75 ml). The solvent is evaporated off under reduced pressure ($T_{bath}$ 35° C., 10 mbar). A pale yellow oil (28.18 g, yield by mass of 97%) is obtained. The molar purity is greater than 85% ($^1$H NMR). Product C is used for the following step without any further purification.

Assignment Table

| | δ $^1$H (ppm) | δ $^{13}$C (ppm) |
|---|---|---|
| 1 | 10.4 | 192.6 |
| 2 | / | 131.2 |
| 3 | / | 133.3 |
| 4 | 2.43 | 12 |
| 5 | / | 153.7 |
| 6 | 3.67 and 3.87 | 71.3 |
| 7 | 3.09 | 61.1 |
| 8 | / | 57.8 |
| 9 | 1.17 and 1.28 | 18.6 and 24.3 |
| 10 | / | 125.8 |
| 11 | 2.21 | 16.5 |
| 12 | 6.79 | 13.5 |
| 13 | / | 136.4 |
| 14 | 2.4 | 19.5 |

Solvent CDCl$_3$

Synthesis of 3-(3,3-dinnethyloxiran-2-yl)methoxy)-2,4,6-trinnethylbenzaldehyde oxime (D)

A solution of hydroxylamine (5.02 g, 0.760 mol, 50% in water, Aldrich) in ethanol (10 ml) is added to a solution of 3-((3,3-dinnethyloxiran-2-yl)methoxy)-2,4,6-trinnethylbenzaldehyde (11.8 g, 0.475 mol) in ethanol (25 ml) at 40° C. ($T_{bath}$). The reaction medium is stirred at 55° C. ($T_{bath}$) for 2.5-3.0 hours. After evaporating off the solvent ($T_{bath}$ 32° C., 26 mbar), a mixture of ethyl acetate (20 ml), petroleum ether (40/60) (30 ml) and water (10 ml) is added. The organic phase is then separated out and washed with water (10 ml). The solution is filtered through a bed of silica gel (0 3.5 cm, h=2.0 cm) and the bed of silica gel is then washed with a mixture of ethyl acetate (10 ml) and petroleum ether (20 ml). After evaporating off the solvents ($T_{bath}$ 33° C., 11 mbar), a colourless oil (10.33 g, yield by mass of 83%) is obtained. The molar purity is greater than 78% ($^1$H NMR) and 16% of EtOAc. Product D is used in the following step without any further drying.

Assignment Table

| | δ $^1$H (ppm) | δ $^{13}$C (ppm) |
|---|---|---|
| 1 | 8.29 | 149.2 |
| 2 | / | 128.3 |
| 3 | / | 129.9 |
| 4 | 2.27 | 13.3 |
| 5 | / | 153.5 |
| 6 | 3.76 and 3.88 | 71.2 |
| 7 | 3.15 | 61.4 |
| 8 | / | 58 |
| 9 | 1.22 and 1.33 | 18.6 and 24.4 |
| 10 | / | 131.3 |
| 11 | 2.22 | 16.1 |
| 12 | 6.83 | 130.5 |
| 13 | / | 132.7 |
| 14 | 2.25 | 20.4 |

Solvent CDCl$_3$

Synthesis of 3-((3,3-dimethyloxiran-2-yl)methoxy)-2,4,6-trimethylbenzonitrile oxide (D-2)

An aqueous solution of NaOCl in water (62.9 g Cl/l) (65 ml) is added dropwise over 15 minutes to a solution of 3-((3,3-dimethyloxiran-2-yl)methoxy)-2,4,6-trimethylbenzaldehyde oxime (9.90 g, 0.367 mol) in dichloromethane (350 ml) cooled to 1-3° C. The temperature of the reaction medium remains between 2-3° C. The reaction medium is then stirred for 2 hours at 2-3° C. The organic phase is separated out and washed with water (three times 50 ml). The solvent is evaporated off under reduced pressure ($T_{bath}$ 21° C., 120 mbar). Petroleum ether (40/60) (15 ml) is added to this residue and the suspension is maintained at −18° C. for 2 hours. The precipitate is filtered off, washed on the filter with petroleum ether (three times 15 ml) and finally dried at atmospheric pressure at room temperature for 10-15 hours. A white solid (4.42 g, yield by mass of 45%) with a melting point of 84° C. is obtained. The molar purity is greater than 98% ($^1$H NMR).

17

Assignment Table

| | δ ¹H (ppm) | δ ¹³C (ppm) |
|---|---|---|
| 1 | / | / |
| 2 | / | 112.7 |
| 3 | / | 134.2 |
| 4 | 2.35 | 14.8 |
| 5 | / | 153.4 |
| 6 | 3.93/3.71 | 71.9 |
| 7 | 3.11 | 61.2 |
| 8 | / | 57.8 |

18

-continued

| | δ ¹H (ppm) | δ ¹³C (ppm) |
|---|---|---|
| 9 | 1.22 and 1.33 | 24.5/18.8 |
| 10 | / | 134.2 |
| 11 | 2.23 | 16.5 |
| 12 | 6.86 | 130.2 |
| 13 | / | 137.2 |
| 14 | 2.32 | 20 |

Solvent CDCl₃

Synthesis of 2,4,6-trimethyl-3-(3-(3-methyloxiran-2-yl)propoxy)benzonitrile oxide (D-3)

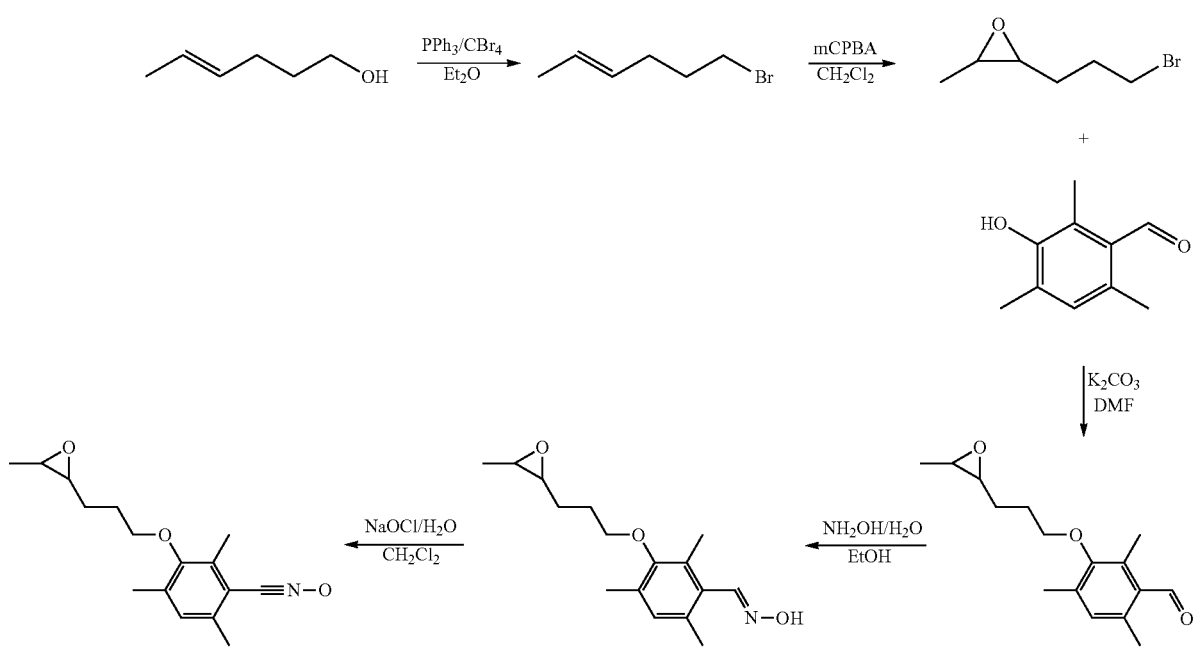

Synthesis of 6-bromohex-2-ene

This compound may be obtained, for example, according to a procedure described in the article Nicolai, Stefano et al. *Tetrahedron,* 71(35), 5959-5964; 2015

Synthesis of 2-(3-bromopropyl)-3-methyloxirane

This compound may be obtained, for example, according to a procedure described in the article Hu, Shanghai; Hager, Lowell P.; *Tetrahedron Letters;* vol. 40; nb. 9; (1999); pages 1641-1644.

Synthesis of 2,4,6-trimethyl-3-(3-(3-methyloxiran-2-yl)propoxy)benzaldehyde

Potassium carbonate (6.01 g, 0.044 mol) is added to a mixture of 3-hydroxy-2,4,6-trimethylbenzaldehyde (10.00 g, 0.061 mol) and 2-(3-bromopropyl)-3-methyloxirane (10.39 g, 0.058 mol) in DMF (5 ml). The reaction medium is stirred at 80° C. ($T_{bath}$) for 1 hour and then at 100° C. ($T_{bath}$) for 3 hours. After returning to room temperature, the reaction mixture is diluted with a mixture of water (75 ml) and methylene chloride (50 ml). The product is extracted with methylene chloride (twice 10 ml). The combined organic phases are washed twice with NaOH solution (4 g in 50 ml of water) and with water (three times with 15 ml). The solvent is evaporated off under reduced pressure ($T_{bath}$ 45°C., 8 mbar). An oil (14.25 g, yield by mass of 93%) is obtained. The molar purity is greater than 85% ($^1$H NMR). The product is used for the following step without any further purification.

Assignment Table

| | δ $^1$H (ppm) | δ $^{13}$C (ppm) |
|---|---|---|
| 1 | 10.46 | 193.2 |
| 2 | / | 131.7 |
| 3 | / | 133.8 |
| 4 | 2.45 | 19.9 |
| 5 | 6.83 | 131.9 |
| 6 | / | 137 |
| 7 | 2.22 | 16.8 |
| 8 | / | 154.4 |
| 9 | / | 136.5 |
| 10 | 2.44 | 12.3 |
| 11 | 3.67 | 72.2 |
| 12 | 1.89 | 26.7 |
| 13 | 1.62-1.79 | 28.7 |
| 14 | 2.66 | 59.3 |
| 15 | 2.75 | 54.5 |
| 16 | 1.25 | 17.6 |

Solvent CDCl$_3$

Synthesis of 2,4,6-trimethyl-3-(3-(3-methyloxiran-2-yl)propoxy)benzaldehyde oxime A solution of hydroxylamine (5.13 g, 0.078 mol, 50% in water, Aldrich) in ethanol (10 ml) is added to a solution of 2,4,6-trimethyl-3-(3-(3-methyloxiran-2-yl)propoxy)benzaldehyde (14.00 g, 0.056 mol) in ethanol (40 ml) at 45° C. The reaction medium is stirred at 50° C. ($T_{bath}$) for 1.5 hours. After evaporating off the solvent ($T_{bath}$ 40° C., 45 mbar), methylene chloride (50 ml) is added and the solution is washed with water (three times 15 ml). After evaporating off the solvent ($T_{bath}$ 40° C., 70 mbar), methylene chloride is then added. The suspension is stirred at room temperature for 10 minutes and cooled to −18° C. for 10-15 minutes. The precipitate is filtered off, washed on the filter three times with a mixture of methylene chloride (1 ml) and petroleum ether (4 ml) and finally dried at atmospheric pressure at room temperature. A white solid (10.02 g, yield by mass of 65%) with a melting point of 78° C. is obtained. The molar purity is greater than 90% ($^1$H NMR).

Assignment Table

| | δ $^1$H (ppm) | δ $^{13}$C (ppm) |
|---|---|---|
| 1 | 1.26 | 17.6 |
| 2 | 2.76 | 54.7 |
| 3 | 2.68 | 59.5 |
| 4 | 1.65/1.79 | 28.8 |
| 5 | 1.88 | 26.8 |
| 6 | 3.68 | 72.0 |
| 7 | / | 154.1 |
| 8 | / | 130.4 |
| 9 | 2.24 | 13.6 |
| 10 | / | 128.4 |
| 11 | 8.30 | 149.9 |
| 12 | / | 132.7 |
| 13 | 2.25 | 20.5 |
| 14 | 6.82 | 130.8 |
| 15 | / | 131.8 |
| 16 | 2.19 | 16.3 |

Solvent CDCl$_3$

Synthesis of 2,4,6-trimethyl-3-(3-(3-methyloxiran-2-yl)propoxy)benzonitrile oxide (D-3)

An aqueous solution of NaOCl in water (4% of active chlorine, Aldrich) (17 ml) is added dropwise over 5 minutes to a solution of 2,4,6-trimethyl-3-(3-(3-methyloxiran-2-yl)propoxy)benzaldehyde oxime (3.35 g, 0.012 mol) in dichloromethane (50 ml) cooled to 0° C. ($T_{bath}$). The temperature of the reaction medium remains between 3 and 5° C. The reaction medium is then stirred for 1 hour at a temperature of 3-5° C. The aqueous phase is separated out and then extracted with dichloromethane (5 ml). The combined organic phases are washed with water (twice 5 ml). The solvent is evaporated off under reduced pressure ($T_{bath}$ 21° C., 16 mbar). Petroleum ether (40/60) (7 ml) is added to this residue and the suspension is stirred at room temperature for 10 minutes. The precipitate is filtered off, washed on the filter with petroleum ether (twice 5 ml) and finally dried at atmospheric pressure at room temperature. A pale yellow solid (2.49 g, yield by mass of 75%) with a melting point of 56° C. is obtained. The molar purity is greater than 94% ($^1$H NMR).

Assignment Table

| | δ $^1$H (ppm) | δ $^{13}$C (ppm) |
|---|---|---|
| 1 | 1.26 | 17.6 |
| 2 | 2.75 | 54.5 |

21
-continued

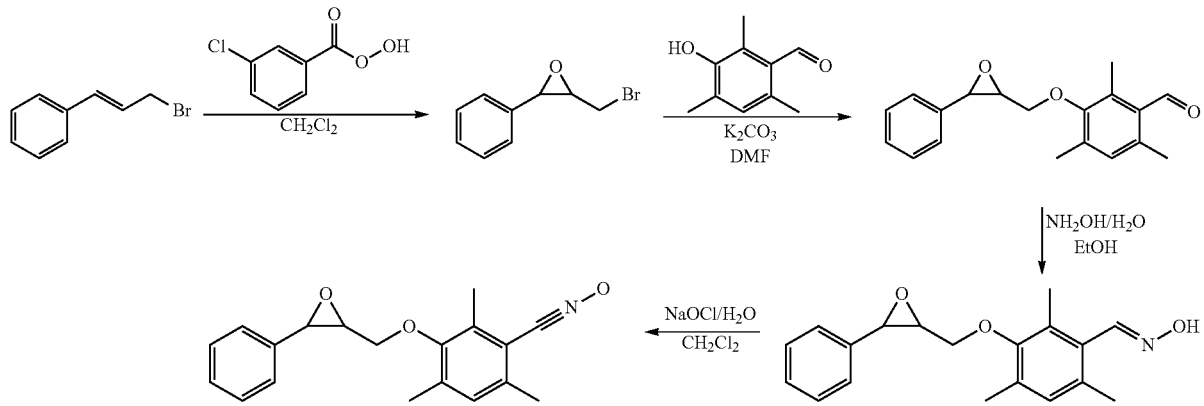

| δ $^1$H (ppm) | δ $^{13}$C (ppm) |
|---|---|
| 3 | 2.66 | 59.3 |
| 4 | 1.60/1.80 | 28.7 |
| 5 | 1.88 | 26.8 |
| 6 | 3.68 | 72.2 |
| 7 | / | 153.9 |
| 8 | / | 137.1 or 134.6 |
| 9 | 2.31 | 14.9 |
| 10 | / | 112.8 |
| 11 | / | / |
| 12 | / | 137.1 or 134.6 |

22
-continued

| δ $^1$H (ppm) | δ $^{13}$C (ppm) |
|---|---|
| 13 | 2.31 | 20.3 |
| 14 | 6.84 | 130.3 |
| 15 | / | 134.6 |
| 16 | 2.19 | 16.5 |

Solvent CDCl$_3$

Synthesis of 2,4,6-trimethyl-3-((3-phenyloxiran-2-yl)methoxy]benzonitrile oxide (D-4)

Synthesis of 2-(bromomethyl)-3-phenyloxirane

This compound may be obtained according to a procedure described in the article Dickinson, Julia M. et al., Chemical Society, Perkin Transactions 1: *Organic and Bio-Organic Chemistry* (1972-1999), (4), 1179-84; 1990.

Synthesis of 2,4,6-trimethyl-3-(3-(3-phenyloxiran-2-yl)methoxy)benzaldehyde

Potassium carbonate (8.51 g, 0.062 mol) is added to a mixture of 3-hydroxy-2,4,6-trimethylbenzaldehyde (13.50 g, 0.082 mol) and 2-(bromomethyl)-3-phenyloxirane (17.50 g, 0.082 mol) in DMF (8 ml). The reaction medium is stirred at 60° C. (T$_{bath}$) for 5-6 hours. After returning to 40-50° C., the reaction mixture is diluted with a mixture of water (200 ml) and ethyl acetate (70-80 ml). The target product is extracted with ethyl acetate (twice 25 ml). The combined organic phases are washed with NaOH solution (8 g in 70 ml of water) and with water (four times 25 ml). The solvent is evaporated off under reduced pressure (T$_{bath}$ 34°C, 16 mbar). Petroleum ether (40/60) (50 ml) is added and the precipitate is filtered off, washed on the filter with a mixture of petroleum ether (15 ml) and ethyl acetate (1 ml) and finally dried at atmospheric pressure at room temperature.

A beige-coloured solid (13.28 g, yield by mass of 55%) with a melting point of 53° C. is obtained. The molar purity is greater than 90% ($^1$H NMR).

Assignment Table

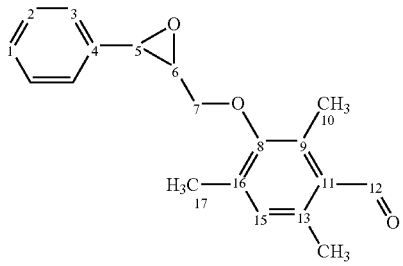

| | δ $^1$H (ppm) | δ $^{13}$C (ppm) |
|---|---|---|
| 1/2 | 7.18 to 7.34 | 128.2/128.3 |
| 3 | | 125.5 |
| 4 | / | 136.2 |
| 5 | 3.81 | 55.9 |
| 6 | 3.35 | 60.2 |
| 7 | 3.84 and 4.04 | 72.5 |
| 8 | / | 153.8 |
| 9/13/16 | / | 132/133.7/136.7 |
| 10 | 2.5 | 12.2 |
| 11 | / | 131.5 |
| 12 | 10.48 | 193 |
| 14 | 2.48 | 19.8 |
| 15 | 6.87 | 131.8 |
| 17 | 2.28 | 16.6 |

Solvent CDCl$_3$

Synthesis of 2,4,6-trimethyl-3-((3-phenyloxiran-2-yl)methoxy)benzaldehyde oxime

A solution of hydroxylamine (1.43 g, 0.022 mol, 50% in water, Aldrich) in ethanol (5 ml) is added to a solution of 2,4,6-trimethyl-3-((3-phenyloxiran-2-yl)methoxy)benzaldehyde (4.60 g, 0.016 mol) in ethanol (20 ml) at 45° C. The reaction medium is stirred at 50° C. (T$_{bath}$) for 1.5 hours. After returning to room temperature, water (3 ml) is added to the suspension and the suspension is maintained at −18° C. for 2 hours. The precipitate is filtered off, washed on the filter with ethanol and water (3 ml/2 ml and 1 ml/4 ml) and finally dried at atmospheric pressure at room temperature. A white solid (3.62 g, yield by mass of 75%) with a melting point of 125° C. is obtained. The molar purity is greater than 97% ($^1$H NMR).

Assignment Table

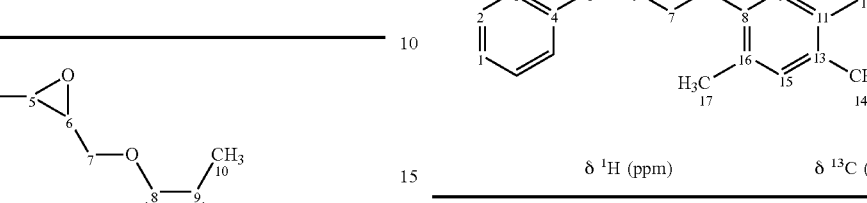

| | δ $^1$H (ppm) | δ $^{13}$C (ppm) |
|---|---|---|
| 1/2 | 7.21 to 7.35 | 128/128.2 |
| 3 | | 125.4 |
| 4 | / | 136.2 |
| 5 | 3.81 | 56 |
| 6 | 3.35 | 60.3 |
| 7 | 3.85 and 4.02 | 72.2 |
| 8 | / | 153.4 |
| 9 | / | 130.2 |
| 10 | 2.29 | 13.1 |
| 11 | / | 128.2 |
| 12 | 8.31 | 149.6 |
| 13 | / | 132.9 |
| 14 | 2.27 | 20.3 |
| 15 | 6.85 | 130.7 |
| 16 | / | 131 |
| 17 | 2.24 | 16 |

Solvent CDCl$_3$

Synthesis of 2,4,6-trimethyl-3-((3-phenyloxiran-2-yl)methoxy]benzonitrile oxide (D-4)

An aqueous solution of NaOCl in water (74.4 g Cl/l) (48 ml) is added dropwise over 15 minutes to a solution of 2,4,6-trimethyl-3-((3-phenyloxiran-2-yl)methoxy)benzaldehyde oxime (10.20 g, 0.033 mol) in dichloromethane (150 ml) cooled to 4° C. The temperature of the reaction medium remains between 3 and 5° C. The reaction medium is then stirred for 2.5 hours at a temperature of 3-5° C. The aqueous phase is separated out and extracted with dichloromethane (15 ml). The combined organic solutions are washed with water (three times 20 ml). The solvent is evaporated off under reduced pressure (T$_{bath}$ 23° C., 22 mbar). Petroleum ether (40/60) (60 ml) is added and the suspension is stirred at room temperature for 10-15 minutes. The precipitate is filtered off, washed on the filter with petroleum ether (twice with 20 ml) and finally dried at atmospheric pressure at room temperature. A white solid (8.35 g, yield by mass of 82%) with a melting point of 64° C. is obtained. The molar purity is greater than 98% CH NMR).

Assignment Table

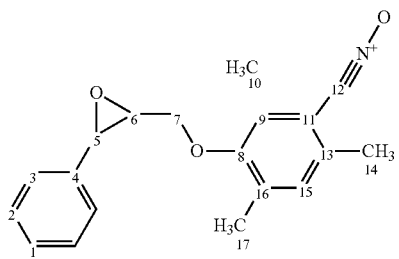

| | δ $^1$H (ppm) | δ $^{13}$C (ppm) |
|---|---|---|
| 1/2 | 7.21 to 7.35 | 128.2/128.4 |
| 3 | | 125.4 |
| 4 | / | 136.1 |
| 5 | 3.79 | 55.8 |
| 6 | 3.33 | 60.1 |
| 7 | 3.82 and 4.05 | 72.5 |
| 8 | / | 153.3 |
| 9/13/16 | / | 130.3/134.4/137.3 |
| 10 | 2.36 | 14.6 |
| 11 | / | 112.8 |
| 12 | / | / |
| 14 | 2.33 | 20.1 |
| 15 | 6.87 | 130.2 |
| 17 | 2.25 | 16.4 |

Solvent CDCl$_3$

II.3—Grafting of the 1,3- Dipolar Compounds

For the grafting agent, use is made of the 1,3-dipolar compounds D-1 to D-4, the synthesis of which is described hereinabove in paragraph 11.2.

The starting polymers are the following elastomers:

E1: a copolymer of 1,3-butadiene and of styrene (SBR) containing 26% of styrene units and 56% of 1,2-butadiene units E2: a copolymer of 1,3-butadiene and of styrene (SBR) containing 26% of styrene units and 24% of 1,2-butadiene units E3: a synthetic polyisoprene with a high cis content, Nipol2200 from Nippon Zeon E4: natural rubber.

The elastomers are modified according to the following procedure:

The 1,3-dipolar compound is incorporated into the elastomer using an internal mixer (roll machine) at 30° C., the amount of compound added is 0.5 mol per 100 mol of diene monomer units of the elastomer. The mixture is homogenized in 15 turnover passes. This mixing phase is followed by a heat treatment at 120° C. for 10 minutes under a press at a pressure of 10 bar.

The grafting yield determined by NMR analysis for each of the elastomers and the 1,3-dipolar compounds is given in the following table:

| Yield | D-1 | D-2 | D-3 |
|---|---|---|---|
| E1 | 75% | 100% | 100% |
| E2 | 100% | 100% | 90% |
| E3 | 38% | 100% | 52% |
| E4 | 30% | 48% | 40% |

II.4—Preparation of the Rubber Compositions

Five rubber compositions T, C-1, C-2, C-3 and C-4, respectively, the formulation of which (in phr) is given in Table I, are prepared.

The elastomer of composition T is an unmodified elastomer, in this instance the starting elastomer E1 used for preparing the modified elastomers of compositions 1 to 4.

Composition T is a control composition, since it contains the starting (unmodified) diene elastomer.

The elastomer of composition C-n (n ranging from 1 to 4) is the elastomer E1 modified in accordance with section ll-3 with the 1,3-dipolar compound D–n.

Composition C-1 is a comparative composition, since the 1,3-dipolar compound used to modify the elastomer of the composition is not in accordance with the invention, the second member of the epoxide ring being neither a tertiary carbon nor a quaternary carbon.

Compositions C-2 to C-4 are in accordance with the invention, since each of the 1,3-dipolar compounds used to modify the elastomer of the compositions is in accordance with the invention by virtue of the presence of a tertiary (compositions 3 and 4) or quaternary (composition 2) carbon other than the carbon atom providing the attachment to the dipole.

The rubber compositions are prepared according to the following procedure:

The elastomer is introduced into an internal mixer, the initial vessel temperature of which is about 80° C., and is kneaded for about 1 minute. The reinforcing filler, the silane and then, after 1-2 minutes of kneading, the various other ingredients, with the exception of the vulcanization system, are then introduced. Thermomechanical working is then performed (non-productive phase) in one step (total duration of the kneading equal to about 5 minutes), until a maximum "dropping" temperature of 145° C. is reached. The mixture thus obtained is recovered and cooled and the vulcanization system (sulfur) is then added on an external mixer (homofinisher) at 25° C., the whole being mixed (productive phase) for about 5 to 6 minutes. The mixture is then calendered in the form of plates (thickness of 2 to 3 mm) for measurement of the tensile properties and of the dynamic properties. The mixture is then vulcanized, and its rheometric properties and cured properties are measured.

The results are given in Table II. The results are indicated in base 100 relative to the control composition (T): the value indicated for a composition being the ratio between the value measured on the composition and the value measured on the control composition.

The vulcanized compositions C-2 to C-4 have an elongation at break and a breaking stress that are improved relative to the composition C-1. These results are obtained without being at the expense of the hysteresis properties, since the ΔG* and Tan (δ) max values remain very much lower than that of the control composition (T). The ΔC values, which are lower than that of composition T, corroborate an improvement in the interaction between the elastomer and the reinforcing filler.

It is also observed that the Cmin values of compositions C-2 to C-4 are lower than that of composition C-1, which indicates a decrease in the viscosity in the uncured state (before vulcanization) of the compositions and suggests the likelihood of implementation of compositions C-2 to C-4 that is at least as easy as that of composition T. This result is all the more surprising since an improvement in the interaction between the elastomer and the reinforcing filler has moreover been found.

In summary, when compared with the compositions not in accordance with the invention, the rubber compositions in accordance with the invention are characterized by an improved compromise between the rupture properties, the hysteresis properties and the implementation properties. The use of the 1,3-dipolar compounds in accordance with the invention in the production of rubber compositions, notably in the step of modifying the elastomer of the rubber composition, thus makes it possible to substantially improve the properties thereof.

TABLE I

| Composition | T | C-1 | C-2 | C-3 | C-4 |
|---|---|---|---|---|---|
| E1 | 100 | | | | |
| E1 modified with D-1 | | 100 | | | |
| E1 modified with D-2 | | | 100 | | |
| E1 modified with D-3 | | | | 100 | |
| E1 modified with D-4 | | | | | 100 |
| Silica (1) | 60 | 60 | 60 | 60 | 60 |
| Silane (2) | 4.8 | 4.8 | 4.8 | 4.8 | 4.8 |
| Antioxidant (3) | 3 | 3 | 3 | 3 | 3 |
| Paraffin (4) | 1 | 1 | 1 | 1 | 1 |
| ZnO (5) | 2.7 | 2.7 | 2.7 | 2.7 | 2.7 |
| Stearic acid | 2.5 | 2.5 | 2.5 | 2.5 | 2.5 |
| CBS (6) | 1.8 | 1.8 | 1.8 | 1.8 | 1.8 |
| Sulfur | 1.5 | 1.5 | 1.5 | 1.5 | 1.5 |

(1) 160 MP silica sold by Solvay
(2) TESPT sold by Evonik under the reference SI69
(3) N-(1,3-dimethylbutyl)-N'-phenyl-p-phenylenediamine from the company Flexsys
(4) Paraffin 6266 processing aid
(5) Zinc oxide
(6) N-cyclohexyl-2-benzothiazolesulfenamide (Santocure CBS from the company Flexsys)

TABLE II

| Composition | T | C-1 | C-2 | C-3 | C-4 |
|---|---|---|---|---|---|
| Elongation at break | 100 | 58 | 84 | 68 | 74 |
| Breaking stress | 100 | 90 | 111 | 97 | 97 |
| ΔG* | 100 | 71 | 79 | 88 | 88 |
| Tan(δ) max | 100 | 73 | 73 | 81 | 73 |
| C min | 100 | 110 | 74 | 74 | 84 |
| ΔC | 100 | 68 | 76 | 94 | 66 |

The invention claimed is:

1. A 1,3-dipolar compound including an epoxide group, the epoxide group being a 3-membered ether ring in which a first member is a carbon atom having an attachment to the dipole of the 1,3-dipolar compound and a second member is a tertiary or quaternary carbon, and the compound being a nitrile monooxide.

2. The 1,3-dipolar compound according to claim 1, in which the epoxide group is of formula (I)

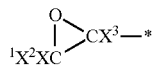

(I)

in which:
* represents an attachment to the dipole,
$X^1$, $X^2$ and $X^3$, which may be identical or different, represent a hydrogen atom or a substituent group, and at least one from among $X^1$, $X^2$ and $X^3$ is other than a hydrogen atom.

3. The 1,3-dipolar compound according to claim 2, in which the substituent group is an alkyl or an aryl.

4. The 1,3-dipolar compound according to claim 1, which comprises a benzene nucleus, which benzene nucleus is substituted with the dipole of the 1,3-dipolar compound.

5. The 1,3-dipolar compound according to claim 4, in which the benzene nucleus is substituted ortho to the dipole.

6. The 1,3-dipolar compound according to claim 1, which compound contains a unit of formula (II)

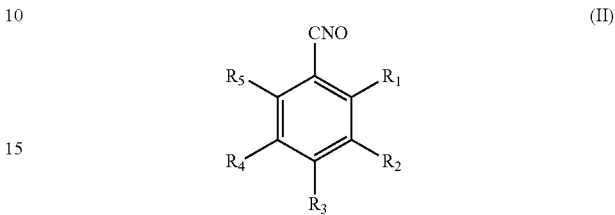

(II)

in which:
four of the five symbols R1 to R5, which may be identical or different, are each an atom or a group of atoms, and the fifth symbol represents a carbon-based chain for attachment to the epoxide group, given that at least one from among R1 and R5 is other than a hydrogen atom.

7. The 1,3-dipolar compound according to claim 6, in which R1, R3 and R5 each represent a hydrocarbon-based group.

8. The 1,3-dipolar compound according to claim 6, in which the fifth symbol represents a carbon-based chain interrupted with one or more heteroatoms.

9. The 1,3-dipolar compound according to claim 6, in which the fifth symbol comprises a —CH$_2$O— group, the methylene group being attached to the epoxide group.

10. The 1,3-dipolar compound according to claim 1, having as formula one of the formulae (III), (IV) or (V)

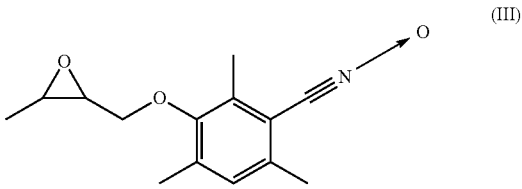

(III)

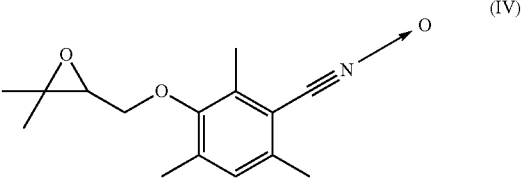

(IV)

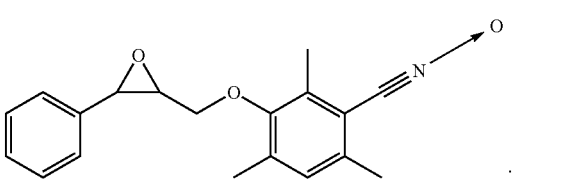

(V)

11. A process for modifying a diene polymer via a grafting reaction, which comprises the reaction of a starting diene polymer and of the 1,3-dipolar compound defined in claim 1.

12. A 1,3-dipolar compound according to claim 6, in which R1, R3 and R5 each represent alkyl.

13. A 1,3-dipolar compound according to claim 6, in which the fifth symbol represents a carbon-based chain interrupted with one or more oxygen.

\* \* \* \* \*